United States Patent
Neff

Patent Number: 5,873,840
Date of Patent: Feb. 23, 1999

[54] INTRACRANIAL PRESSURE MONITORING SYSTEM

[76] Inventor: Samuel R. Neff, 600 Fairview Rd., Narberth, Pa. 19072

[21] Appl. No.: 915,778

[22] Filed: Aug. 21, 1997

[51] Int. Cl.$^6$ ........................................................ A61B 5/00
[52] U.S. Cl. ............................ 600/561; 600/587; 343/767
[58] Field of Search ................................... 600/561, 587, 600/595; 343/700, 767

[56] References Cited

U.S. PATENT DOCUMENTS

| | | |
|---|---|---|
| 3,853,117 | 12/1974 | Murr . |
| 3,943,915 | 3/1976 | Severson . |
| 3,977,391 | 8/1976 | Fleischmann . |
| 4,003,141 | 1/1977 | Le Roy . |
| 4,014,319 | 3/1977 | Favre . |
| 4,026,276 | 5/1977 | Chubbuck . |
| 4,062,354 | 12/1977 | Taylor et al. . |
| 4,114,606 | 9/1978 | Seylar . |
| 4,127,110 | 11/1978 | Bullara . |
| 4,186,749 | 2/1980 | Fryer . |
| 4,206,761 | 6/1980 | Cosman . |
| 4,206,762 | 6/1980 | Cosman . |
| 4,246,908 | 1/1981 | Inagaki et al. . |
| 4,265,252 | 5/1981 | Chubbuck et al. . |
| 4,281,667 | 8/1981 | Cosman . |
| 4,354,506 | 10/1982 | Sakaguchi et al. . |
| 4,378,809 | 4/1983 | Cosman . |
| 4,471,786 | 9/1984 | Inagaki et al. . |
| 4,494,411 | 1/1985 | Koschke et al. . |
| 4,593,703 | 6/1986 | Cosman . |
| 4,653,508 | 3/1987 | Cosman . |
| 4,660,568 | 4/1987 | Cosman . |
| 4,676,255 | 6/1987 | Cosman . |
| 4,738,267 | 4/1988 | Lazorthes et al. . |
| 4,926,696 | 5/1990 | Haritonidis et al. . |
| 5,018,529 | 5/1991 | Tenerz et al. . |
| 5,317,917 | 6/1994 | Dufour . |

*Primary Examiner*—Max Hindenburg
*Assistant Examiner*—Pamela J. Wingood
*Attorney, Agent, or Firm*—Caesar, Rivise, Bernstein, Cohen & Pokotilow, Ltd.

[57] ABSTRACT

A system for monitoring intracranial pressure by an implantable cavity resonator unit and an associated externally located transceiver unit. The resonator unit includes a dielectric-filled cavity having a predetermined resonance frequency for high frequency electromagnetic waves. The cavity is bounded by a wall having a pair of intersecting slots forming a slot antenna and a deflectable diaphragm in communication with the interior of the cranium to deflect as a function of intracranial pressure. The deflection alters the resonance frequency of the cavity. The transceiver unit includes a linear wave guide having a pair of electrically conductive probes located in it. At least one of the probes is arranged to transmit an electromagnetic excitation wave from an associated transmitter through the slot antenna to cause the cavity to resonate at an altered resonance frequency, whereupon a resonance wave is reflected out of the cavity through the slot antenna. At least a second of the probes picks up the resonance wave and provides it to a receiver which provides an electrical signal indicative of the reflected wave. This signal is representative of the intracranial pressure. The cavity is sealed to prevent the ingress of body fluids therein.

18 Claims, 4 Drawing Sheets

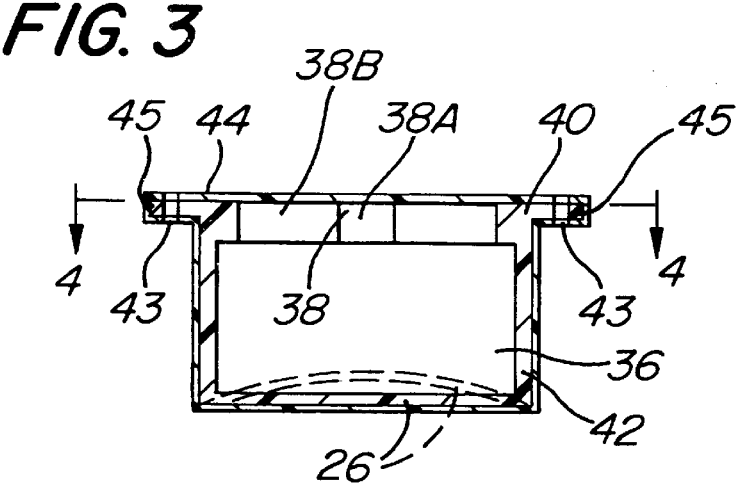
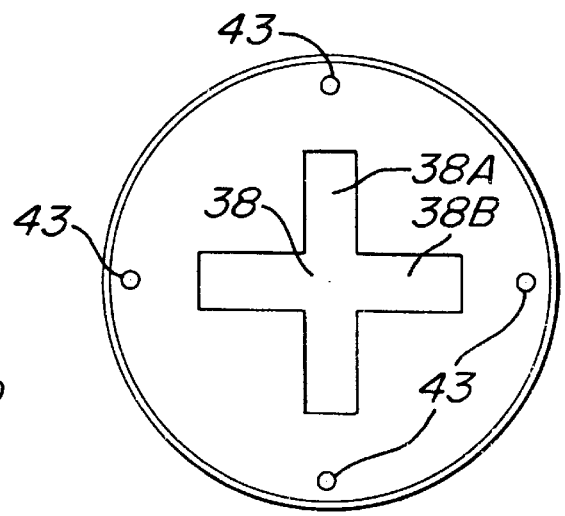
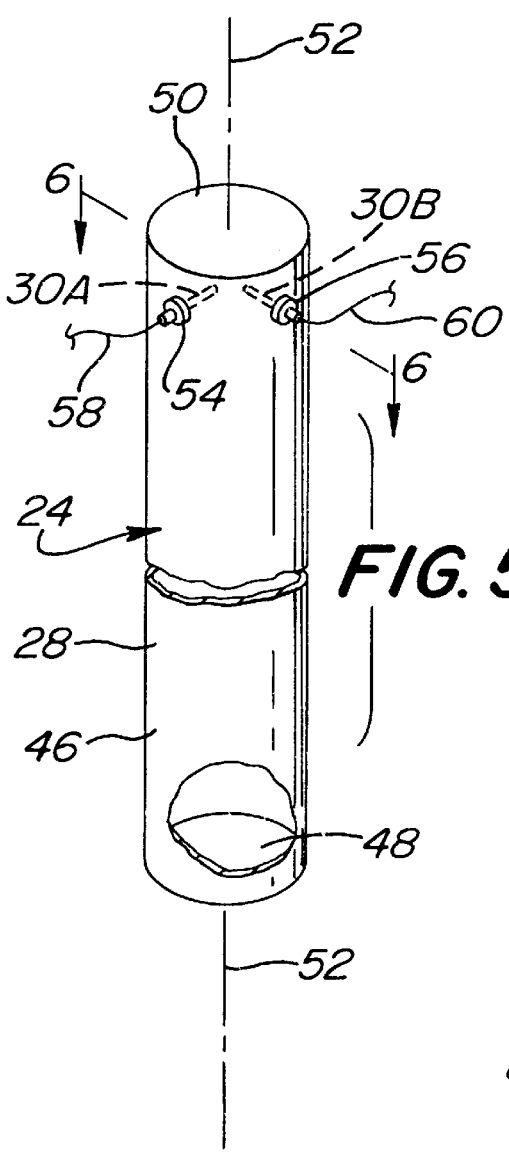
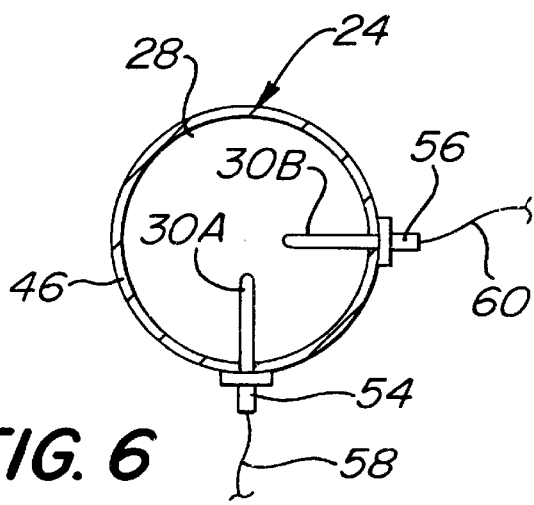

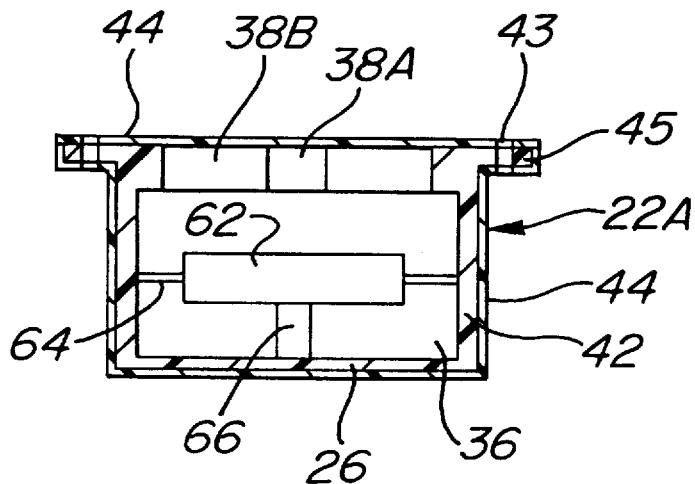
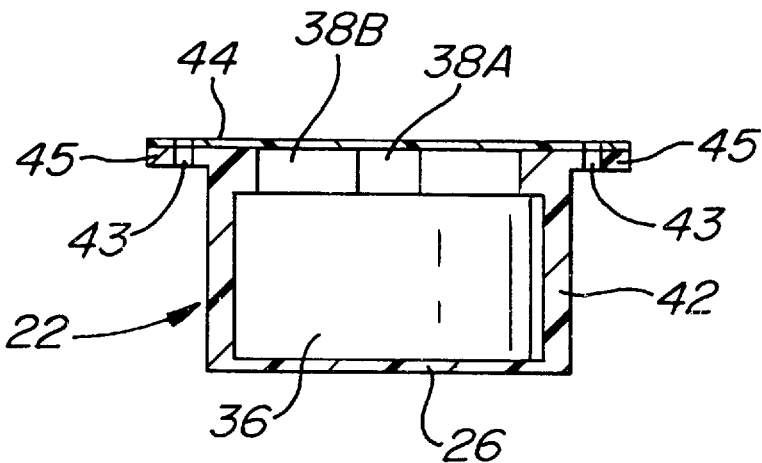
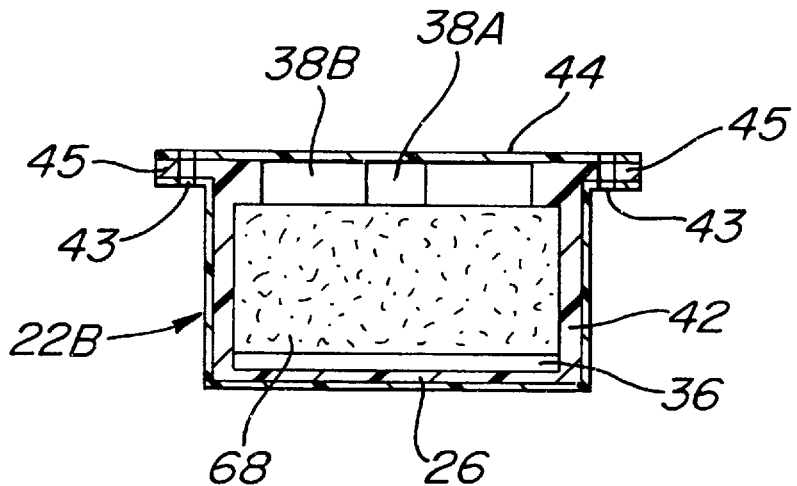

INTRACRANIAL PRESSURE MONITORING SYSTEM

BACKGROUND OF THE INVENTION

This invention relates generally to medical devices and more particularly to systems for monitoring intracranial pressure of a living being.

Numerous patents have been issued disclosing various means for monitoring intracranial pressure by means of an implant to sense such pressure and provide a signal representative thereof to some externally located means. The following constitutes United States Patents relating to such technology:

U.S. Pat. No. 3,853,117 (Murr) discloses a pressure-sensing system and method which makes use of ultrasound to interrogate a deformable, implantable device.

U.S. Pat. No. 3,943,915 (Severson) discloses an intracranial pressure monitoring device which incorporates a lumped-constant tuned circuit, with a capacitor whose plate separation varies as a function of pressure.

U.S. Pat. No. 3,977,391 (Fleischmann) discloses a pressure sensor apparatus which uses a radionuclide source in an arrangement with shielding that provides for variable ionizing radiation output with applied pressure. The device includes a mechanical or hydraulic motion amplification system, with associated moving parts.

U.S. Pat. No. 4,003,141 (LeRoy) discloses several intracranial pressure sensors, including an implantable one that is based on the external detection of a change in a magnetic field when an implanted sensor incorporating a magnet is deformed.

U.S. Pat. No. 4,014,319 (Favre) discloses an intracranial pressure transducer using an implanted magnet to vibrate in an externally applied magnetic field, the frequency of vibration varying according to the pressure.

U.S. Pat. No. 4,026,276 (Chubbuck) discloses an intracranial pressure monitor in the form of an implantable intracranial sensor using a metal bellows containing a gas as the deforming element. This element is linked to one plate of a capacitor in a lumped-constant tuned circuit.

U.S. Pat. No. 4,062,354 (Taylor et al.) discloses an intracranial pressure transducer system using an implanted active circuit including a power receiver and tunnel-diode oscillator.

U.S. Pat. No. 4,114,606 (Seylar) discloses a monitoring apparatus for resonant circuit intracranial pressure implants. The apparatus includes a resonance-detection device for use with implantable resonant circuits, like those described in U.S. Pat. No. 4,026,276. An external monitoring circuitry in the form of an RF sweep generator is provided to monitor its own output.

U.S. Pat. No. 4,127,110 (Bullara) discloses an implantable pressure transducer incorporating a sliding bearing and a fluid-filled link to the intracranial space.

U.S. Pat. No. 4,186,749 (Fryer) discloses an induction powered biological radiosonde in the form of a variable capacitor pressure transducer as part of a tuned circuit. The tuned circuit varies the frequency of an induction-powered oscillator.

U.S. Pat. No. 4,206,761 (Cosman) discloses a pressure-balanced telemetric pressure sensing method.

U.S. Pat. No. 4,206,762 (Cosman) discloses a telemetric differential pressure sensing method using a flexible polymer membrane and a sliding bearing. Most of the embodiments described require that the scalp transmit atmospheric pressure faithfully to the device.

U.S. Pat. No. 4,246,908 (Inagaki et al.) discloses an intracranial pressure transducer based on a piezo-electric or semiconductive pressure sensor. This device is not a permanently implantable, nor a remote device.

U.S. Pat. No. 4,265,252 (Chubbuck et al.) discloses an intracranial pressure implant using a bellow and a capacitive pressure sensor.

U.S. Pat. No. 4,281,667 (Cosman) discloses a single diaphragm telemetric differential pressure sensing system which appears to be an improvement of the system of U.S. Pat. Nos. 4,206,761 and 4,206,762.

U.S. Pat. No. 4,354,506 (Sakaguchi et al.) discloses an intracranial pressure gauge. This patent describes both variable capacitor and variable inductor methods of detecting the deflection of a diaphragm using a lumped-constant tuned circuit.

U.S. Pat. No. 4,378,809 (Cosman) discloses audio-telemetric pressure sensing systems and acoustic methods of interrogating the sensors like those of U.S. Pat. Nos. 4,281,667, 4,206,761 and 4,206,762.

U.S. Pat. No. 4,471,786 (Inagaki et al.) discloses a telemetering intracranial pressure transducer which requires an internal battery for power, a pressure-transmitting flexible plastic membrane and a complex active circuit.

U.S. Pat. No. 4,494,411 (Koschke et al.) discloses a pressure detector comprising a cylindrical cavity resonator having a front surface made as a diaphragm and using a coaxial cavity with a helical winding and ceramic core. The device requires an active circuit within it and a highly elastic, conductive metal diaphragm.

U.S. Pat. No. 4,593,703 (Cosman) discloses a telemetric differential pressure sensor with the improvement of a conductive shorted loop tuning element and a resonant circuit, e.g., an implantable tuned circuit having a deflectable diaphragm with the inductive element coupled to the diaphragm.

U.S. Pat. No. 4,653,508 (Cosman) discloses a pressure-balanced telemetric pressure sensing system and method. The system requires the placing of a pressure transducer against a detection chamber which has been implanted just under the scalp. The detection chamber is connected via a fluid path to the intracranial space.

U.S. Pat. No. 4,660,568 (Cosman) discloses a telemetric differential pressure sensing system and method making use of an implanted flexible plastic membrane, a fluid channel, and a sliding bearing. In some embodiments, capacitive or inductive coupling through the scalp is used.

U.S. Pat. No. 4,676,255 (Cosman) discloses a telemetric in-vivo calibration method and apparatus using a negative pressure applicator. This patent discloses a way to calibrate an implanted sensor of the type described in U.S. Pat. Nos. 4,660,568, 4,378,809, 4,281,667, 4,206,761 and 4,206,762.

U.S. Pat. No. 4,738,267 (Lazorthes et al.) discloses an implantable, intracranial-pressure sensor, in the form of a resistive strain gauge which is not self-contained.

U.S. Pat. No. 4,926,696 (Haritonidis et al.) discloses an optical micropressure transducer which requires a clear optical path to and from the sensing element.

U.S. Pat. No. 5,018,529 (Tenerz et al.) discloses a miniaturized sensor for physiological pressure measurements which utilizes external illumination delivered by an optical fiber and returns its signal through that fiber.

U.S. Pat. No. 5,317,917 (Dufour) discloses a resonant pressure transducer in the form of a mechanical resonant circuit whose characteristic frequency of mechanical vibration varies according to ambient pressure.

While the prior art intracranial pressure sensing devices and equipment like those described above, may be generally suitable for their intended purposes, they never the less leave much to be desired from the standpoints of complexity, cost, durability, range, sensitivity and reliability.

OBJECTS OF THE INVENTION

Accordingly, it is a general object of this invention to provide a system which overcomes the disadvantages of the prior art.

It is a further object of this invention to provide an intracranial pressure monitoring system which is simple in construction.

It is a further object of this invention to provide an intracranial pressure monitoring system which is relatively low in cost.

It is a further object of this invention to provide an intracranial pressure monitoring system making use of a readily implantable unit.

It is still a further object of this invention to provide an intracranial pressure monitoring system making use of an implantable unit which is biocompatible, suitable for long-term use and which doesn't present a hazard to the patient if it fails.

It is yet a further object of this invention to provide an intracranial pressure monitoring system suitable for continuous, unsupervised, ambulatory monitoring.

SUMMARY OF THE INVENTION

These and other objects of the subject invention are achieved by providing a system for monitoring the pressure within the cranium of a living being (e.g., a human). The system comprises an cavity resonator and an associated transceiver. The cavity resonator is a hollow member (e.g., formed of metal), defining an interior cavity and having a first wall in the form of a deflectable diaphragm and a second wall including slot antenna means (e.g., a pair of linear slots extending perpendicularly to each other and through which electromagnetic waves can freely pass) and a cover over the slot antenna to prevent the ingress of body fluids into the interior of the cavity through the slot antenna.

The cavity resonator has a predetermined resonance frequency for high frequency electromagnetic waves (e.g., approximately 10 GHz) and is arranged to be implanted within the being's cranium so that the deflectable diaphragm is in communication with the interior of the cranium. The diaphragm is arranged to be deflected in response to the pressure within the being's cranium, whereupon the resonance frequency is changed as a function of that pressure.

The transceiver (e.g., an electrical transmitter, an elongated linear wave guide, an electrical receiver, and a pair of electrically conductive linear probes) is arranged to be located outside of the cranium of the being. The transceiver (e.g., the transmitter and at least one probe coupled to it) is arranged to transmit a high frequency electromagnetic excitation wave through the slot antenna means (e.g., the first slot) into the cavity to cause the cavity to resonate at an altered resonance frequency, whereupon a resonance wave is reflected out of the cavity through the slot antenna means (e.g., the second slot). The transceiver includes means (e.g., a probe and a receiver) for receiving the resonance wave and for providing an electrical signal indicative thereof. The electrical signal is indicative of the second (e.g., reflected) wave is thus representative of the intracranial pressure.

In accordance with one preferred aspect of the invention the system utilizes linearly polarized electromagnetic waves, while in another preferred aspect it utilizes circularly polarized waves.

DESCRIPTION OF THE DRAWING

Other objects and many attendant features of this invention will become readily appreciated as the same becomes better understood by reference to the following detailed description when considered in connection with the accompanying drawing wherein:

FIG. 3 is an enlarged sectional view of the cavity resonator unit taken along line 3—3 of FIG. 2;

FIG. 4 is an enlarged sectional view of the implantable cavity resonator unit taken along line 4—4 of FIG. 3;

FIG. 5 is an enlarged isometric view, partially in section, of the transceiver unit shown in an FIGS. 1 and 2;

FIG. 6 is an enlarged sectional view taken along line 6—6 of FIG. 5;

FIG. 7 is a sectional view, similar to FIG. 3, but showing an alternative embodiment of an implantable cavity resonator unit of this invention;

FIG. 8 is a sectional view, similar to FIGS. 3 and 7, but showing another alternative embodiment of an implantable cavity resonator unit of this invention;

FIG. 9 is a sectional view, similar to FIGS. 3, 7 and 8, but showing still another alternative embodiment of an implantable cavity resonator unit of this invention;

DETAILED DESCRIPTION OF THE PREFERRED EMBODIMENTS

Figure 1:
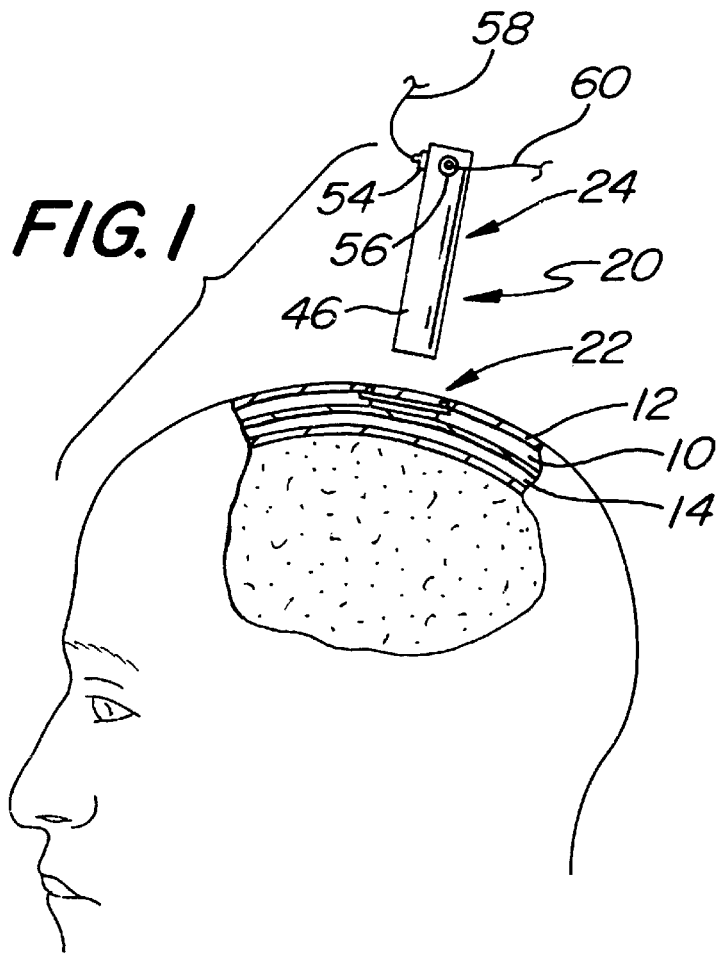
FIG. 1 is an illustration showing one embodiment of the system of this invention in use for determining the intracranial pressure of a living human being.
Figure 2:
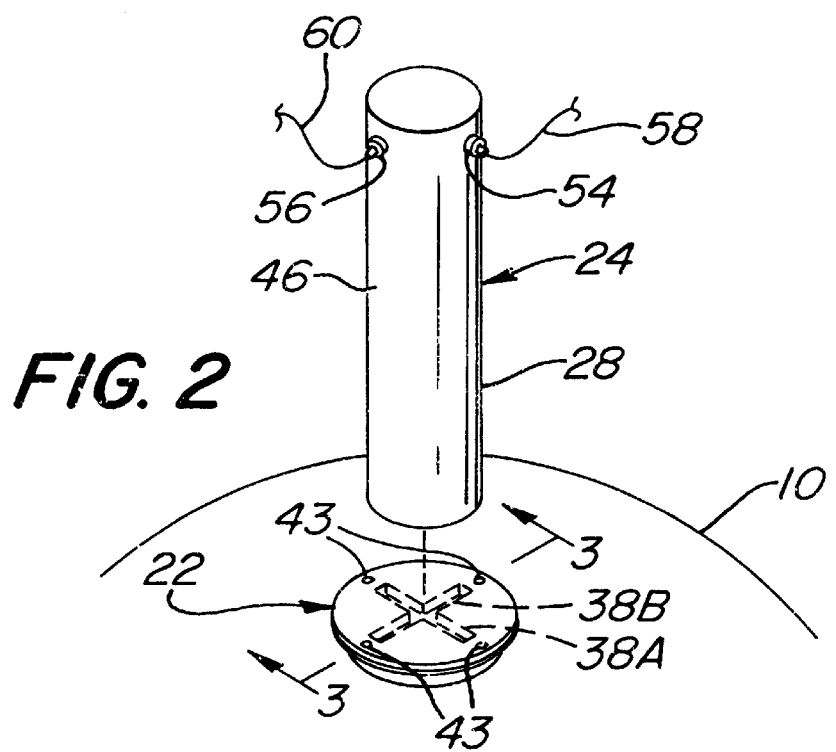
FIG. 2 is an enlarged exploded isometric view of the transceiver unit and the implantable cavity resonator unit of the system shown in FIG. 1.

Referring now to the drawing where like reference numerals refer to like parts there is shown at 20 in FIG. 1 a system constructed in accordance with this invention for monitoring or determining the intracranial pressure of a living being. The system 20 basically includes an implantable cavity resonator unit 22 and an associated transceiver unit 24. The cavity resonator unit is arranged to be implanted within an opening drilled into the cranium 10 of the being, so that it is located below the scalp 12 and with a portion of the cavity resonator unit, i.e., a deflectable diaphragm 26 (FIG. 3—to be described later), in communication with the interior 14 of the cranium and the pressure extant therein. The transceiver unit is in the form of a waveguide 28 having a pair of electrically conductive probes 30A and 30B mounted therein, an associated transmitter 32 and receiver 34. As will be discussed in detail later the probes 30A and 30B extend perpendicularly to each other.

Depending upon the embodiment of the invention, a least one of the probes, e.g., probe 30A, is electrically connected to the transmitter 32. The transmitter 32 is arranged for producing a high frequency, e.g., 10 GHz, electromagnetic excitation wave and for providing it to the probe, e.g., probe 30A. The waveguide 28 propagates the excitation wave into the implanted cavity resonator unit 22. The other of these probes, e.g., probe 30B, is connected to the receiver 34 and is arranged to pick up the resonance wave (to be described later) from the cavity resonator unit. This wave is coupled from the probe 30B to the receiver 34. The receiver 34 provides an electrical output signal which is indicative or representative of the resonance wave and the intracranial pressure.

The details of the construction and operation of the cavity resonator unit 22 will be described later. Suffice it for now to state that, as is known, the cavity resonator unit 22 comprises an enclosure having electrically conductive walls surrounding a dielectric medium, e.g., air, dry nitrogen gas, a vacuum, etc., and which is capable of resonating with high frequency electromagnetic waves, e.g., microwaves or ultra-high frequency waves. The enclosure has at least one opening or window, e.g., the slot antenna 38 (to be described later) for coupling the electromagnetic energy between the inside and outside of the cavity.

Only waves of certain discrete frequencies can exist within the cavity. These "allowed" frequencies are a function of the size and shape of the cavity and other factors, e.g., they must be solutions of Maxwell's equations. When subjected to electromagnetic waves having an excitation frequency of an allowed value or values the cavity will resonate at a resonance frequency or narrow range of frequencies. The resulting resonance waves may be picked up or received through the window by any suitable receiving means, e.g, at least one of the probes 30A and 30B. The value of the resonant frequency(ies) depend(s) upon the size, shape, dielectric material, and the "mode" of the wave, e.g., the type of transverse electric (TE) mode of the wave.

As is known, a TE mode of operation is the mode which the electric intensity of the electromagnetic wave has only one component transverse, i.e., perpendicular, to the direction of wave propagation. The simplest and most commonly used mode of wave propagation is the so-called $TE_{01}$ mode. As will be discussed hereafter the preferred embodiments of this invention make use of a cavity resonator having a cavity 36 (FIG. 3) whose depth (i.e., the dimension in the direction of wave propagation) is equal to one quarter of the wavelength of the excitation wave at which resonance occurs. Moreover, the cavity 36 is preferably of circular cylindrical shape.

A cavity which has a small energy loss is commonly referred to as a "high-Q" cavity and is generally preferred. Circular cylindrical cavities, like those of the subject invention, are particularly useful for obtaining higher Q's than rectangular cavities, particularly when operating in the $TE_{01}$ mode.

The details of the construction and operation of the waveguide 28 will also be described later. Suffice for now to state that as used herein a "Waveguide" is an electrically conductive, e.g., metallic, tube which confines and guides the propagation of electromagnetic waves down its length. Only unique patterns or modes, e.g., a $TE_{01}$ mode, of the electrical field distribution are possible within a hollow waveguide with a given cross section which is uniform along its entire length. The waveguide 28 is also preferably of circular cylindrical shape, although it can be of any regular, symmetrical cross-sectional shape, e.g., square, rectangular, etc. As will be appreciated by those skilled in the art a circular cylindrical tube, like the preferred embodiment of waveguide 28, can sustain waves of all kinds of field polarization, e.g., linear, circular, and elliptic, because of its circular cylindrical symmetry.

The waveguide 28 is arranged to provide the high frequency excitation wave through the slot antenna 38 (to be described later) forming one wall 40 of the cavity resonator. The wall 40 is located opposite the diaphragm 26, with the circular cylindrical cavity 36 being defined between the wall 40, the diaphragm 26 and a cylindrical side-wall 42 (to be described later).

As mentioned above the diaphragm 26 is arranged to be in communication with the interior 14 of the cranium 10 when the cavity resonator is in place. Since the diaphragm 26 is deflectable the intracranial pressure will cause the diaphragm to move from its normal, unbiased, position to a new or "ambient pressure position". This position (shown by the exaggerated phantom lines in FIG. 3) is thus a function of the existing intracranial pressure. The movement of the diaphragm to the ambient pressure position changes the size and shape of the cavity 36, thereby altering its resonant frequency(ies). Accordingly, the resonance wave picked up by the probe, e.g, probe 30B, of the wave guide 28 and which is provided to the receiver 34 will be indicative of the intracranial pressure. The receiver provides an output signal, e.g., an electrical signal, which can be used by associated means (to be described later) for displaying the monitored intracranial pressure.

As can be seen in FIG. 4, the slot antenna 38 basically comprises a pair of equal length slots 38A and 38B in the top wall 40 of the cavity resonator. These slots intersect at right angles to each other to form a cruciform-shaped slot antenna. This arrangement facilitates discrimination between the resonance wave reflected from the interior of the cavity resonator unit from those electromagnetic waves which may be reflected from other, spurious, sources, e.g., the scalp tissue 12. This action is accomplished by polarizing the exciting and resonance waves. In particular, when the waveguide is held at a desired orientation with respect to the implanted cavity resonator, the excitation wave propagated from one of the perpendicularly oriented probes, e.g., probe 30A, enters the cavity resonator through one of the slots, e.g., 38A, while the resonance wave exits from the other of those slots, e.g., 38B. Thus, the resonance wave will be polarized 90 degrees from the excitation wave. If the orientation of the waveguide is not changed with respect to the implanted cavity resonator (and it likely will not over the short period of time during which a measurement is taken) the receiving probe, i.e., the probe connected to the receiver 34, will pick up the polarized resonance wave since it is aligned with that wave. Thus, the receiver's receiving probe will be more sensitive to the polarized resonance wave from the implanted cavity resonator than it is to an excitation wave reflected from the scalp tissue since the reflected excitation wave will be oriented 90 degrees from it, i.e. will be aligned with the other probe from which the excitation wave emanated.

In the one preferred embodiment of the invention for providing an excitation wave of a frequency of approximately 10 GHz, the top wall of the cavity resonator is preferably approximately 1.2 cm in diameter (the diaphragm 26 is the same diameter) and the height of the cavity, i.e., the spacing between the top wall and the diaphragm, is equal to one quarter of the wavelength of that wave (i.e., approximately 0.8 mm). Each slot 38A and 38B is in the range of approximately 0.8 to 1 cm in length and in the range of approximately 0.5 mm to 2 mm in width.

In order to prevent the ingress of any body fluid, e.g., blood, intracranial fluid, etc., a fluid-impervious covering or coating 44, e.g., medical grade silicone rubber, such as that sold under the trademark SILASTIC, is provided over the slots. This covering, while being fluid-impervious is never the less transparent to the electromagnetic waves so that they can pass freely through it. Other materials can be used for the barrier covering, e.g., PTFE. The covering 44 may be provided over the entire exterior surface of the cavity resonator unit, as shown in FIG. 3 or may be confined to the top wall 40 over the slots 38A and 38B as shown in FIG. 8.

The cavity resonator unit may be secured in place by means of plural mounting holes 43 in a flange 45 forming the periphery of the top wall 40. Sutures (not shown) or other holding means, e.g., screws (not shown), can be extended through the holes 43 to secure the cavity resonator unit in place.

As can be best seen in FIGS. 5 and 6, one preferred embodiment of the waveguide 28 is an elongated linear cylindrical tube 46 formed of an electrically conductive metal whose inside diameter is approximately ¾ inch (19 mm). The tube 46 is open at its distal end 48 and is closed at its proximal end 50. Each of the probes 30A and 30B is a linear, electrically conductive wire whose length is equal to ¼ of the wavelength of the excitation wave. Thus, for a 10 GHz excitation wave the length of each probe 30A and 30B is 7.5 mm. The probes 30A and 30B are disposed perpendicularly to each other in a common plane which extends perpendicularly to the longitudinal axis 52 of the waveguide tube 46. This results in a linearly polarized wave. Alternatively, the probes 30A and 30B may be located different planes which are separated from each other by ¼ the wavelength of the excitation wave to provide a circularly polarized signal. A circularly polarized signal may also be produced by a waveguide having both probes 30A and 30B extending perpendicularly to each other and lying in a common plane by including a quarter wavelength delay line in the electrical circuitry connected to either of the probes.

As can be seen in FIG. 6, the probes 30A and 30B are mounted in the interior of the waveguide tube adjacent its closed end 50 by conventional electrical connectors, e.g., SMA connectors, 54 and 56, respectively. An electrical conductor or wire 58 is connected via the SMA connector 54 to the transmitter 32 to electrically interconnect the probe 30A and the transmitter. A similar electrical conductor or wire 60 is connected via the SMA connector 56 to the receiver 34 to electrically interconnect the probe 30B and the receiver.

The transmitter 32 is in the form of any suitable source of high frequency electrical signals, and is preferably adjustable or sweepable to enable the selection of the frequency of the signal(s) to be provided by it to the probe 30A to cause the cavity resonator to resonate at the existing intracranial pressure. In particular, the transmitter 32 is swept over the frequency range that the particularly sized and shaped cavity resonator would be expected to resonate at for an intracranial pressure within a range of physiological interest. For living human beings the range of intracranial pressure of interest physiologically is from 0–30 torr (mm Hg). Thus, utilizing the cavity resonator described heretofore the excitation electromagnetic wave is swept through a range of 10 GHz to 10.25 GHz for a pressure on the resonator's diaphragm 26 of 0–30 torr (mm Hg).

The transmitter 32 is preferably swept through this range in a short period of time at a relatively repetition high rate, e.g., 10 Hz, in order to minimize the chance of any relative movement between the waveguide 28 and the cavity resonator which could adversely affect the measurement, and to desensitize the apparatus to the effects of intracranial pressure changes. The chance of relative movement between the waveguide 28 and the implanted cavity resonator can be eliminated by providing some support means, e.g., a stand, helmet or some other means, to hold the waveguide 28 in a fixed position with respect to the implanted cavity resonator.

One particularly suitable transmitter is a Gunn-diode oscillator (10 mW), such as that sold by Advanced Receiver Research as Part #MA-87127-1.

Figure 10:
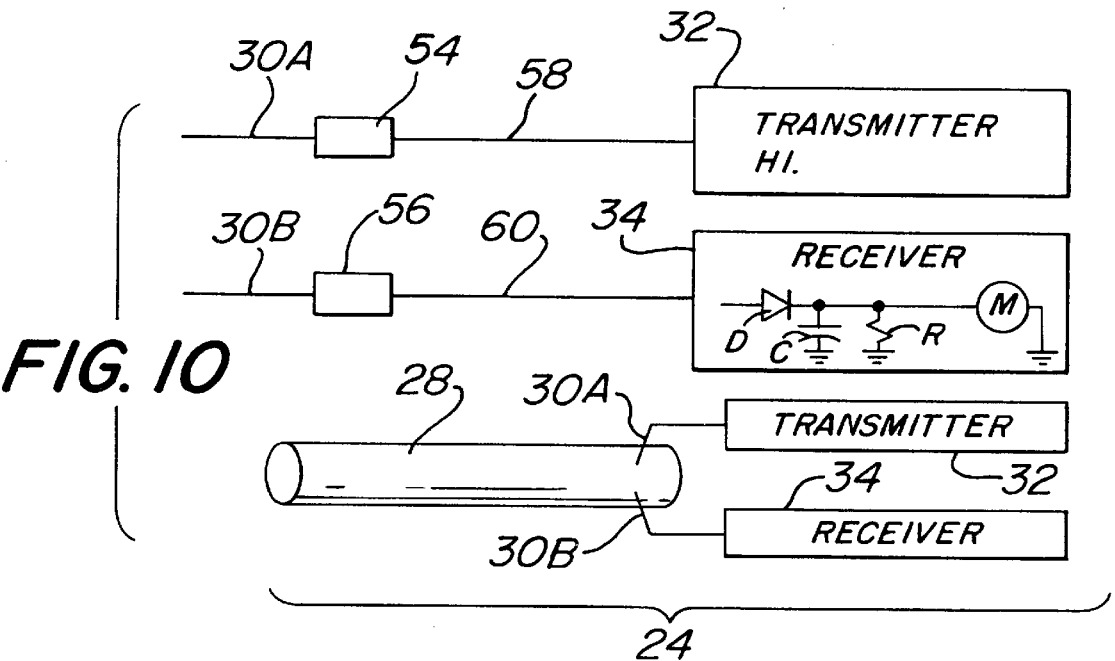
FIG. 10 is a hybrid diagram, partially schematic and partially mechanical, showing the embodiment of the transceiver portion of the system shown in FIG. 1.

The details of the receiver 34 are shown in FIG. 10. As can be seen therein the receiver basically comprises a diode D, a capacitor c, a resistor R and a volt meter M. One particularly suitable diode is that sold by Hewlett Packard Company as crystal detector, Part No. X421A. The anode of the diode D is connected to the conductor 60 from the probe 30B. The cathode of the diode is connected to the juncture of one side of the resistor R and one side of the meter M. The other side of the resistor is connected to ground. The other side of the meter is also connected to ground. Any suitable low current (e.g., milliamp) volt meter (e.g., one having a range of 0–1 volt) can be used.

As will be appreciated by those skilled in the art, the resonance electromagnetic wave received by the probe 30B produces a corresponding electrical signal, which signal is coupled via the diode D and associated resistor R to the volt meter M. The voltmeter provides a visual indication of the voltage of the received signal, which voltage is indicative of the intracranial pressure. Alternatively, the electrical signal representative of the resonance wave, and hence the intracranial pressure, can be provided to some other device(s). For example, the analog signal from the receiving probe can be provided to an analog-to-digital (A/D) converter and from there to any suitable digital device, e.g., a microprocessor, a printer, a modem, etc.

Figure 11:
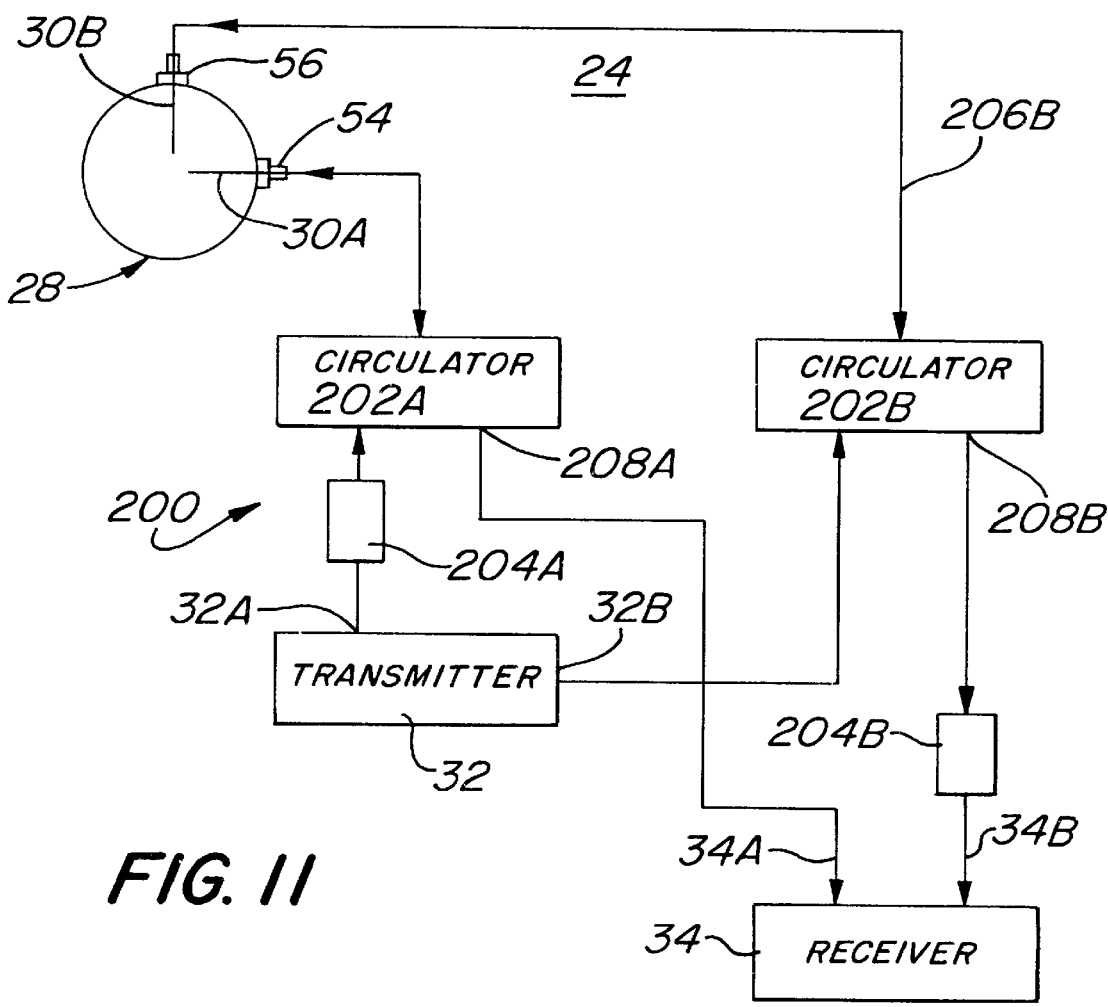
FIG. 11 is a hybrid diagram, similar to FIG. 10, but showing an alternative embodiment of the transceiver portion of the system of this invention.

In FIG. 11 there is shown an alternative embodiment of a system of this invention. This embodiment of the system is denoted by the reference number 200 and produces circularly polarized electromagnetic excitation waves from a pair of probes. In particular, the system 200 provides the excitation waves from both probes, with the waves from the probes being offset from each other by a quarter of the wavelength of the excitation wave.

As can be seen in FIG. 11, the embodiment 200 utilizes the same cavity resonator unit 22, the same waveguide 28 and probes 30A and 30B, and the same transmitter 32 and receiver 34 as discussed earlier. However, the manner in which the transmitter 32 and receiver 34 of the transceiver are connected to the probes are different. In the interests of brevity and drawing simplicity the common components between the systems 20 and 200 will be given the same reference numbers and the details of their construction and operation will not be reiterated. Thus, as can be seen the transmitter 32 includes a pair of output lines 32A and 32B. The receiver includes a pair of input lines 34A and 34B. The transceiver 24 also includes an pair of identical circulators 202A and 202B, and a pair of identical delay lines 204A and 204B. The circulators 202A and 202B are conventional 3port devices, like that sold by Micromega as Part #22021. Each of the delay lines can take any form suitable for delaying the electrical wave passing therethrough by a quarter of its wavelength. Thus, the delay lines may be made up by an electrical conductor or wire of a length equal to one quarter of the wavelength of the wave to pass therethrough.

Each of the two output lines 32A and 32B of the transmitter 32 are arranged to carry the electromagnetic excitation waves produced by the transmitter to the two probes 30A and 30B. In particular, the output line 32A is connected to one side of the delay line 204A. The other side of the delay line 204A is connected to one terminal of the circulator 202A. Another terminal of the circulator is connected via a conductor or wire 206A to the probe 30A. The other output line 32B of the transmitter is connected to one terminal of the circulator 202B. Another terminal of the circulator 202B is connected via a conductor or wire 206B to the probe 30B. Each of the delay lines is arranged to delay the electromagnetic wave passing through it by one quarter of its wave length. Thus, the electromagnetic excitation wave provided to probe 30A will be delayed by one quarter of its wavelength from the excitation wave provided to probe 30B. These circularly polarized excitation waves will be provided by the waveguide to the cavity resonator 22 in the same manner as described earlier to cause the cavity to resonate and provide circularly polarized resonance waves.

The receiver 34 of the system 200 is arranged to receive the circularly polarized resonance waves from both of the probes 30A and 30B. To that end, another terminal 208A of the circulator 202A is connected to the input 34A of the receiver. Thus, the resonance wave picked up by probe 30A will be provided to the receiver via the circulator 202A. Another terminal 208B of the circulator 202B is connected to one side of the delay line 204B. The other side of the delay line 204B is connected to the other input 34B of the receiver 34. Thus, the resonance wave picked up by probe 30B will be provided to the receiver via the circulator 202B and the delay line 204B, so that that wave will be offset from the wave at input 34A by one quarter of a wavelength. Accordingly, the receiver 34 will be sensitive to signals of the opposite polarization to that produced by the transmitter 32.

As will be appreciated by those skilled in the art by arranging the transceiver as just described the orientation of the probes with respect to the slots of the slot antenna 38 is not as important as with the linearly polarized embodiment of the system 20 described heretofore, since the excitation waves will pass into the cavity resonator unit through both of the slots 38A and 38B, and the resonance waves will pass out of that cavity through both of the slots.

In accordance with one anticipated use of the invention, either embodiment of the system can be constructed and arranged for monitoring the intracranial pressure of a person over an extended period of time, e.g., a day or more, while the person conducts his/her normal day-to-day activities. Such a long-term monitoring system preferably includes some supporting or mounting means, e.g., a helmet (not shown), to hold either the entire transceiver or at least its waveguide in position over the implanted cavity resonator. In addition, a microprocessor-based controller (not shown) located either in the supporting means or in some other means (not shown) to be worn or carried by the patient is coupled to the receiver. The microprocessor-based controller includes associated software to control the operation of the transceiver, e.g., to cause it to operate to take plural intracranial pressure measurements at preselected periods of time, and to either store the measured data or to transmit that data to some remote location, via telemetry, modem or any other suitable electrical transmission means. A small printer may also be included in the system to provide a hard copy record or chart of the acquired data.

It must be pointed out at this juncture that the subject invention can make use of other high frequency excitation waves than the heretofore discussed 10 GHz waves, depending upon the size and shape of the cavity resonator, the physiology of the patient into which the cavity resonator will be implanted, and various other factors known to those skilled in the art. In addition the system may be operated in modes other than the heretofore identified $TE_{01}$ mode. Thus, the system can be operated at higher modes, with a concomitant higher Q's for each such higher mode.

In FIGS. 7 and 9, there is shown alternative embodiments of cavity resonator units of the subject invention. For example, the cavity resonator unit 22A shown in FIG. 7 is identical in construction to that described heretofore except for the dielectric material within its cavity 36. In this regard in the embodiment 22 described heretofore with respect to FIGS. 3 and 8, the dielectric material within the interior of the cavity is a gas, e.g., air, dry nitrogen, etc., or a vacuum. In the embodiment of FIG. 7, the dielectric is a solid, e.g., a ceramic, material exhibiting a higher dielectric permeability than that of air, nitrogen or a vacuum. The use of a higher dielectric constant material enables one to operate the system at substantially higher modes than the $TE_{01}$ mode described above, with concomitantly higher Q's. One particularly effective high dielectric constant material is Barium Titinate. Thus, as can be seen, a block 62 of such a material is mounted generally centered within the interior cavity 36 of the cavity resonator unit 22A. The means for mounting the ceramic block 62 may be an edge mount 64 or a pedestal 66 or a combination of both. If desired, the block of the high dielectric material may be dimensioned to fill up substantially all of the interior cavity of the cavity resonator except for a very small space immediately adjacent the diaphragm 26, to enable the diaphragm to deflect into that space in response to the intracranial pressure. Such an embodiment of the cavity resonator is shown in FIG. 9. In that embodiment, the block of high dielectric material is designated by the reference number 68 and is mounted within the cavity 36 so that only a thin portion of space of cavity 36 remains located contiguous with the diaphragm 26.

As should be appreciated from the foregoing, the implantable cavity resonator units of the systems of this invention each have a very low parts count, i.e., they can be assembled from between three and eight component parts and two or three materials, all with known biocompatibility and a track record of long-term intracranial implantation. Moreover, the transceiver is also of simple construction and low parts count.

Without further elaboration the foregoing will so fully illustrate my invention that others may, by applying current or future knowledge, adopt the same for use under various conditions of service.

What is claimed is:

1. A system for monitoring the pressure within the cranium of a living being, said system comprising an cavity resonator means and transceiver means, said cavity resonator means being a hollow member defining an interior cavity and having a first wall in the form of a deflectable diaphragm, and a second wall including slot antenna means, said cavity resonator means having a predetermined resonance frequency for high frequency electromagnetic waves and being arranged to be implanted within the cranium of the being, whereupon said deflectable diaphragm is in communication with the interior of the being's cranium, said deflectable diaphragm being arranged to be deflected in response to the pressure within the being's cranium to alter said resonance frequency, said transceiver means being arranged to be located outside of the cranium of the being and having means for transmitting a high frequency electromagnetic excitation wave through said slot antenna means into said cavity to cause said cavity to resonate at an altered resonance frequency, whereupon a resonance wave is reflected out of said cavity, said transceiver means having means for receiving said resonance wave and for providing an electrical signal indicative thereof.

2. The system of claim 1 wherein said slot antenna means comprises a first linear slot oriented along a first axis and a second linear slot oriented along a second axis, and whereupon said transceiver means is arranged to transmit said excitation wave through said first slot into said cavity and to receive said resonance wave from said cavity through said second slot.

3. The system of claim 2 wherein said slots are oriented perpendicularly to each other.

4. The system of claim 2 wherein said transceiver means comprises a first electrically conductive linear probe oriented in a first direction and a second electrically conductive linear probe oriented in a second direction, said first probe being arranged to transmit said excitation wave therefrom, said second probe being arranged to receive said resonance wave.

5. The system of claim 3 wherein said transceiver includes a first electrically conductive linear probe oriented in a first direction and a second electrically conductive linear probe oriented in a second direction perpendicular to said first direction, said first probe being arranged to transmit said excitation wave, said second probe being arranged to receive said resonance wave.

6. The system of claim 1 wherein said interior cavity includes a dielectric material in the form of a solid which fills a portion of said cavity and is supported within said cavity by support means.

7. The system of claim 1 wherein said interior cavity includes a dielectric material in the form of a solid which fills substantially all of said cavity except for a portion located immediately adjacent said diaphragm.

8. The system of claim 1 wherein said cavity resonator comprises cover means to prevent the ingress of any body fluid into said interior cavity through said slot antenna means when said cavity resonator is implanted within the being's cranium while enabling said waves to pass freely through said slot antenna means.

9. The system of claim 4 wherein said transceiver means comprises a tubular wave guide having a longitudinal axis, said wave guide having a first open end and a second end, said first and second probe means being located within said wave guide adjacent said second end.

10. The system of claim 9 wherein said first and second probe means are disposed in a common plane extending perpendicular to said longitudinal axis of said waveguide.

11. The system of claim 10 wherein said first and second probe means are oriented perpendicularly to each other.

12. The system of claim 4 wherein said transceiver means comprises a transmitter for providing said excitation wave to said first probe means, and a receiver for receiving said resonance wave from said second probe means.

13. The system of claim 12 wherein said receiver provides said electrical signal indicative of the being's intracranial pressure.

14. The system of claim 1 wherein said first and second walls are spaced on opposite sides of said cavity by approximately one quarter the wavelength of said excitation wave.

15. The system of claim 5 wherein said first probe means is disposed in a first plane and said second probe means is disposed in a second plane, said planes extending parallel to each other and perpendicularly to said longitudinal axis, said planes being spaced from each other by a predetermined distance.

16. The system of claim 15 wherein said predetermined distance is equal to one quarter of the wavelength of said excitation wave.

17. The system of claim 3 wherein said transceiver means comprises a transmitter for providing said excitation wave, a first electrically conductive linear probe oriented in a first direction, a second electrically conductive linear probe oriented in a second direction, and a receiver, said first probe being coupled to said transmitter to transmit said excitation wave therefrom, said second probe being coupled to said transmitter to also transmit said excitation wave therefrom but delayed by a quarter of a wavelength of said excitation wave from said first probe, said first probe being coupled to said receiver and arranged to receive said resonance wave and provide it to said receiver, said second probe being coupled to said receiver and arranged to also receive said resonance wave and to provide it to said receiver but delayed by a quarter of a wavelength of said resonance wave from said first probe.

18. The system of claim 1 additionally comprising securing means for securing said cavity resonator means within the being's cranium.

* * * * *